(12) United States Patent
Coffey et al.

(10) Patent No.: US 8,642,072 B2
(45) Date of Patent: Feb. 4, 2014

(54) MEMBRANE

(75) Inventors: Peter Coffey, London (GB); Lyndon Da Cruz, London (GB); Karen Cheetham, Hertfordshire (GB)

(73) Assignee: UCL Business PLC, London (GB)

( * ) Notice: Subject to any disclaimer, the term of this patent is extended or adjusted under 35 U.S.C. 154(b) by 0 days.

(21) Appl. No.: 12/933,694

(22) PCT Filed: Apr. 8, 2009

(86) PCT No.: PCT/GB2009/000917
§ 371 (c)(1),
(2), (4) Date: Oct. 20, 2010

(87) PCT Pub. No.: WO2009/127809
PCT Pub. Date: Oct. 22, 2009

(65) Prior Publication Data
US 2011/0236464 A1 Sep. 29, 2011

(30) Foreign Application Priority Data
Apr. 14, 2008 (GB) .................................. 0806746.4

(51) Int. Cl.
*A61K 35/12* (2006.01)
(52) U.S. Cl.
USPC ........... 424/443; 424/93.7; 435/396; 435/401
(58) Field of Classification Search
None
See application file for complete search history.

(56) References Cited

FOREIGN PATENT DOCUMENTS

WF 2003/014337 * 2/2003 .............. C12N 5/16

OTHER PUBLICATIONS

Stenzel et al ("Towards Prosthetic Replacement of Bruch's Membrane: Comparison of Polyester and Electrospun Nanofiber Membranes," Invest Ophthalmol Vis Sci 2007;48: E-Abstract 5085 2007).*

Corning (Corning Life Sciences Catalog, 12mm Transwell® with 0.4pm Pore Polyester Membrane Insert, Sterile (Product #3460).*
DeBoer et al ("Multiparameter Analysis of Primary Epithelial Cultures Grown on Cyclopore Membranes," the Journal of Histochemistry and Cytochemistry, 42(2): 277-282 (1994).*
Kannan et al ("Stimulation of apical and basolateral vascular endothelial growth factor-A and vascular endothelial growth factor-C secretion by oxidative stress in polarized retinal pigment epithelial cells," Molecular Vision 2006; 12: t649-59) [Kannan].*
Stanzel et al ("Culture of Human RPE From Aged Donors on a Potential Bruch's Membrane Prosthesis," Invest Ophthalmol Vis Sci 2006;47: E-Abstract 1407 2006)) [Stanzel 2006].*
Algvere et al ("Transplantation of RPE in age-related macular degeneration: observations in disciform lesions and dry RPE atrophy," Graefe's Arch Clin Exp Ophthalmol (1997) 235; 149-158).*
Geisen et al ("Choroidal endothelial cells transmigrate across the retinal pigment epithelium but do not proliferate in response to soluble vascular endothelial growth factor," Experimental Eye Research. 82(4): 608-619 (2006)).*
Corning Product Profile Sheet "Transwell Permeable Supports", (Transwell product 3419) pp. 1-8, 2010-2012) [Corning 2].*
Transwell 2007.*
Binder,Susanne et al: "Transplantation of the RPE in AMD", Progress in Retinal and Eye Research vol. 26, No. 5, Sep. 2007, pp. 516-554.
Stanzel, et al.: "Culture of human RPE from aged donors on a potential Bruch's membrane prosthesis", Invest. Ophthalmol. Vis. Sci., vol. 47, 2006.
"12 mm Transwell with 0.4 um pore polyester membrane insert," retrieved from the Internet: Corning.com Lifesciences.
Stanzel, et al: "Towards prosthetic replacement of bruch's membrane: comparison of polyester and electrospun nanofiber membranes," Invest. Ophthalmol. Vis. Sci., vol. 48, 2007.
Kannan, Ram et al: "Stimulation of apical and basolateral VEGF-A and VEGF-C secretion by oxidative stress in polarized retinal pigment epithelial cells, "Molecular Vision 2006, vol. 12, 2006, pp. 1649-1659.
De Boer, W. et al: "Multiparameter analysis of primary epithelial cultures grown on cyclopore membranes," Journal of Histochemistry and Cytochemistry, 1994, vol. 42, pp. 277-282.

* cited by examiner

*Primary Examiner* — Suzanne Ziska
(74) *Attorney, Agent, or Firm* — Banner & Witcoff, Ltd.

(57) ABSTRACT

The invention relates to a membrane for supporting cells, especially RPE cells. The membrane is useful in the treatment of conditions such as age related macular degeneration.

24 Claims, 4 Drawing Sheets

MEMBRANE

FIELD OF THE INVENTION

The invention relates to a membrane for supporting the growth of cells. Also, the invention relates to methods for growing the cells, producing the membrane and using the cells. In particular the cells may be used in the treatment of age related macular degeneration.

BACKGROUND TO THE INVENTION

Age related macular degeneration (AMD) is a condition found in elderly adults in which the macula area of the retina suffers thinning, atrophy and bleeding. This results in the loss of vision in the central area of vision, particularly an inability to see fine details, to read or to recognise faces.

AMD is classified as either dry (non-neovascular) or wet (neovascular). Wet AMD involves the growth of new blood vessels in an area where they are not supposed to be. The dry form is more common than the wet, with about 85-90 percent of AMD patients diagnosed with dry AMD. The wet form of the disease usually leads to more serious vision loss.

Dry AMD is an early stage of the disease, and may result from the aging and thinning of macular tissues, depositing of pigment in the macula, or a combination of the two processes. Dry macular degeneration is diagnosed when yellowish spots known as drusen begin to accumulate from deposits or debris from deteriorating tissue primarily in the area of the macula. Gradual central vision loss may occur with dry macular degeneration.

Dry AMD can progress to wet AMD, in which new blood vessels grow beneath the retina and leak blood and fluid. This leakage causes permanent damage to light-sensitive retinal cells, which die off and create blind spots in central vision.

Treatments for AMD are at present limited, but some treatments may delay its progression or improve vision. Treatments for macular degeneration depend on whether the disease is in its early stage or dry form or more advanced, wet form that can lead to serious vision loss. One treatment method is the transplantation of cells from the healthy periphery of the eye in patients with wet AMD into the affected area. Whilst this is effective, there is a limit to the size of the affected area that can be treated and the operation is long and inappropriate for most elderly patients. It would be advantageous to provide improved treatments for both forms of AMD.

The inventors have investigated ways that replacement retinal epithelial cells may be obtained and transplanted, in particular using stem cells to produce the required cells. The inventors have developed a membrane on which such cells may be grown and which may be transplanted into the eye, along with the cells. The membrane is particularly useful for the growth of retinal pigmented epithelial (RPE) cells and derivatives thereof, but other cells types may also be grown.

Previously, cells have been grown on membranes. Williams et al., (Journal of Materials Science: Materials in Medicine 16 (2005) 1087-1092) have used polyurethane membranes to culture RPE cells, but have found that the surface of the membranes usually requires treatment to enable cell attachment. Other groups have used polyester membranes.

SUMMARY OF THE INVENTION

According to the invention, there is provided a membrane for supporting the growth of cells, the membrane being substantially non-biodegradable and porous, the pores being between approximately 0.2 µm and 0.5 µm in diameter. Preferably the pore diameter is between 0.3 µm to 0.45 µm.

The membrane is non-biodegradable to ensure that it remains to support the cells once transplanted into the eye. By the term substantially non-biodegradable, it is meant that the membrane does not degrade for at least 5 years following insertion into the body, more preferably at least 10 years, even more preferably at least 15 years.

The pores are of this diameter to allow the diffusion of all nutrients and proteins whilst preventing migration of cells through the polymer.

The pore density is preferably between approximately $1 \times 10^7$ and $3 \times 10^8$ pores per cm, more preferably between $5 \times 10^7$ and $1 \times 10^8$ pores per cm. This density allows the desired permeability levels and also allows vascularisation. In particular the size and density of the pores is important in order to allow the movement of nutrients from one side of the membrane to the other and also allow vascularisation through the membrane. This is especially important post implantation. The polymer body can receive vascularisation from the rich choroidal bed. This has been shown in rich vascular beds outside the eye (Cassell et al, 2002; Patrick et al, 1999; Saxena et al 1999, Peter et al 1998) but can only occur if the porosity is sufficient enough (Menger et al, 1990).

Preferably the membrane hydraulic conductance is more than $50 \times 10^{-10}$ m sec$^{-1}$ Pa$^{-1}$. Specifically, the membrane hydraulic conductance of the membrane is preferably approximately 33 mL/min/cm$^2$. This is equal to $=801.21 \times 10^{-10}$ m sec$^{-1}$ Pa$^{-1}$ which is eight times the hydraulic conductivity of young macular cadaveric Bruch's membrane. This surplus conductivity is useful since the artificial membrane relies entirely on passive processes. As well as being able to meet the demands of the overlying cells in terms of nutrient diffusion, it must also not be a hindrance to fluid transport from the basal side of the RPE layer otherwise the RPE will detach from the polymer surface. This makes sense since reduced hydraulic conductivity of Bruch's membrane in the elderly has been hypothesised to cause pigment epithelial detachments in AMD (Bird & Marshall, 1986).

Preferably, the membrane may be sterilised by gamma irradiation, ethylene oxide, autoclaving or UV sterilization without degrading.

Preferably the membrane may be sealed by ultrasonic sealing, radio frequency sealing or insert moulding. The allows other layers to be attached to the membrane, for example attaching pharmaceutical or coating layers to the membrane. For example, one might wish to attach a more rigid biodegradable layer, such as PLGA, to provide rigidity to the membrane to aid delivery. Alternatively, layers may be attached which contain pharmacological or biological agents, or layers which support other cells.

The membrane preferably has a maximum thickness of approximately 11 µm. More preferably the membrane thickness is between 9 µm and 11 µm. The thickness of the membrane is selected so as to allow diffusion of nutrients, to allow vascularisation and also to allow the membrane to be easily inserted into the eye.

Accordingly, there is provided a membrane for supporting the growth of cells, the membrane being substantially non-biodegradable and porous and having a maximum thickness of approximately 11 µm. The membrane is preferably substantially planar and its smallest dimension is preferably less than approximately 11 µm. It may vary in thickness in that dimension, but is preferably between 9 µm and 11 µm thick.

The membrane preferably has a maximum weight of approximately 1.5 mg/cm$^2$. More preferably the weight of the membrane is between 1.0 mg/cm$^2$ and 1.4 mg/cm$^2$. The minimum tensile strength of the membrane is preferably 100 bars, to provide enough strength to allow properly during surgery. The maximum tensile strength is preferably 300 bars, again to allow the membrane to be handled easily during surgery. The burst strength of the membrane is preferably at least 10 psi.

Preferably, the membrane is hydrophilic. This gives the membrane good wetting capability and allows attachment of cells and other desirable coatings with ease.

The membrane preferably has a pH of 4 to 8, that is a physiologically acceptable pH.

The membrane preferably comprises a coating on at least one side. The coating is preferably a protein or a glycoprotein, such as laminin, matrigel, collagen, fibronectin and PLGA polylactic-co-glycolic acid). The coating may also comprise a pharmacological or biological agent, bound to the coating component. For example, the coating may include a neurotrophic agent, an anti-inflammatory agent, or an antiangiogenic agent.

In particular the coating preferably contains laminin, especially laminin-1 or a fragment thereof, such as IgVAV. In particular, the coating preferably contains more laminin-1 than other protein or glycoprotein. Preferably the coating comprises at least 30%, more preferably at least 40% laminin, especially laminin-1. The coating is preferably applied to produce a laminin-1 concentration on the membrane of approximately 40-45 µg/cm$^2$.

Accordingly, there is provided a membrane for supporting the growth of cells, the membrane comprising a substantially non-biodegradable and porous support layer coated on at least one side with a coating comprising laminin-1.

The membrane is preferably made from a hydrophilic polymer. Also hydrophobic polymers that have been made hydrophilic by shining UV light onto that polymer may be used. Particularly preferred polymers include polyesters such as polyethylene terephthalate, polybutylene terephthalate; polyurethanes and polyurea-urethanes, in particular those containing polycarbonate and polysiloxane, and those that are polyester based or polyether based; polyamides such as nylon; polyether-esters such as Sympatex; polycarbonates such as Makrolon; polyacrylates such as Perspex; poly(tetrafluoroethene) (PTFE); polysiloxanes; polyolefins such as polyethylene and polypropylene; and polyoxymethylene (POM), commonly known under DuPont's brand name Delrin. It is particularly preferred that the membrane is made from polyethylene terephthalate or polybutylene terephthalate. In another preferred embodiment, the membrane is made from polyester.

The membrane is useful for growing a layer of cells. The membrane preferably comprises a layer of cells on the membrane. The cells are may be any cells selected according to the intended use of the membrane and cells. The cell types are any cells that can be grown as a monolayer and include retinal cells, skin cells and endothelial cells and induced pluripotent stem cells. The cells may originate from a variety of sources, for example, the cells may be autologous cells, taken from an individual for transplant back into that individual or may be cells grown specifically for the intended purpose. The cells may have originated from stem cells, particularly human embryonic stem cells. Where the cells have originated from embryonic stem cells, it is preferable that the cells are available from a non-embryonic source, such as a cell bank. In a preferred embodiment, human embryonic stem cells are embryonic pluripotent stem cells. More preferably, the human embryonic stem cells of the invention are obtained by means other than the destruction of human embryos such as the method of isolating hESC disclosed in Lonza et al, Nature, 444:481-485, November 2006. The cells may be immortalised cells such as ARP-19 cells In particular, this invention is useful for the treatment of degenerative diseases, particularly of the retina. Accordingly, the cells may be retinal pigmented epithelial cells (RPE cells), or related cells, such as cells that differentiate to form RPE cells or which are formed from the differentiation of RPE cells (retinal derivatives) or precursors thereof. Such cells may include photoreceptor cells, horizontal cells, amacrine cells or retinal ganglion cells. Other highly differentiated cells may also be used.

The membrane and layer of cells are preferably at least 3 mm×5 mm in length and width. Preferably the membrane and layer of cells are at least 4 mm×6 mm.

When applying the cells to the membrane, it is advantageous to seed the cells densely, in order to reduce the likelihood of the cells de-differentiating. Ideally, the cells should be seeded at a density of at least 200000 cells per cm$^2$, more preferably at around 250000 cells per cm$^2$, or a higher density such as 300000 or 350000 cells per cm$^2$.

Accordingly, there is provided a porous, non-biodegradable membrane for supporting a colony of cells, the membrane having a layer of cells on at least one side, the cells being seeded at a density of at least 200000 cells per cm$^2$.

Also provided is a method of seeding cells onto a membrane comprising the step of seeding the cells onto the membrane at a density of 200000 cells per cm$^2$ or greater.

The membrane is preferably a membrane according to the invention. Further, the cells are preferably highly differentiated cells, such as RPE cells.

Also provided by the invention is the use of a membrane according to the invention, to support a colony of cells.

Further provided is a membrane according to the invention, for use in therapy. In particular, the use of the membrane in the treatment of age related macular degeneration, retinal tears, macular distrophy, choroidemia, Leber Congenital Amarosis and Stargardt Disease is provided.

Also provided is a method for cultivating cells comprising the steps of:
a) seeding human embryonic stem cells with mitomycin C inactivated mouse embryonic fibroblast (MEF) feeders with seeding density of at least 1.2×10$^4$/cm$^2$ or human fibroblast feeders with seeding density of at least 6×10$^3$/cm$^2$; and
b) maintaining the cells in a medium comprising the following components or equivalents thereof: High glucose (4.8 g/L) Knockout Dulbecco's Modified Eagle's Medium (DMEM, Invitrogen) with 20% Knockout serum replacement (Invitrogen), 1% non-essential amino acid solution, 1 mM L-Glutamine (Invitrogen), 4 ng/ml human bFGF (Invitrogen) and 0.1 mM β-mercaptoethanol (Sigma).

The growing cells are preferably fed every two days. At ten days post passage, the feeding regime is preferably changed to a daily feeding routine, using a medium without human basic fibroblast growth factor.

The growing cells are preferably cultured for at least 30 days, more preferably at least 35 days.

The culture medium preferably comprises at least 15%, more preferably at least 18% or at least 20% KSR. Further, the medium preferably does not comprise plasmanate, human LIF and/or bFGF.

The cells form pigmented foci. The foci are preferably removed and placed onto an extracellular matrix in order to allow attachment and expansion of the monolayer.

The invention will now be described in detail by way of example only with reference to the drawings.

DETAILED DESCRIPTION OF THE INVENTION

Example 1

Preparation of the Membrane

Figure 1A:
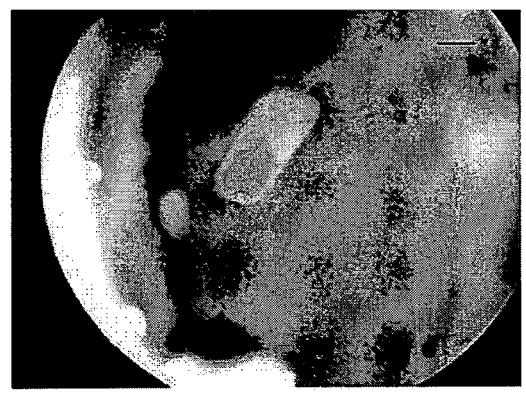
FIG. 1 shows Biopolymer patch with HESC-RPE in situ in the pig eye one month after transplantation (A). B: Light micrograph of A showing photoreceptors with inner/outer segments adjacent to HESC-RPE on biopolymer. C: Polymer alone grafted into pig eye, photoreceptors have degenerated. Stain: cresyl violet. Scale bars: A, 1 mm; B, 100 µm. This demonstrates the biocompatibility of the polymer in vivo and that the monolayer of RPE cells is essential to maintain viable photoreceptors

Thin polyester film is exposed to collimated, charged particles from a nuclear reactor. As these particles pass through the polyester material, they leave sensitized tracks. Next, the polymer tracks are dissolved with an etching solution to form cylindrical pores. Varying the temperature and strength of the etching solution, and the exposure time to it, produces precisely controlled pore sizes.

The resulting membrane is a thin, translucent, microporous polyester film with a smooth, flat surface containing pores of controlled diameter and number.
Production of Human Retinal Pigmented Epithelial Cells (hRPE) from Human Embryonic Stem Cells (hESC)
Cell Culture The hESC are maintained in flasks coated with 0.1% Gelatine and seeded with mitomycin C inactivated mouse embryonic fibroblast (MEF) feeders (with seeding density of $1.2 \times 10^4/cm^2$) or equivalent human fibroblast feeders. Cells are maintained in basic HESC-medium which consists of the following components: High glucose (4.8 g/L) Knockout Dulbecco's Modified Eagle's Medium (DMEM, Invitrogen) with 20% Knockout serum replacement (Invitrogen), 1% non-essential amino acid solution, 1 mM L-Glutamine (Invitrogen), 4 ng/ml human bFGF (Invitrogen) and 0.1 mM β-mercaptoethanol (Sigma). Once removed from cryopreservation, the HESC lines are maintained for up to 74 passages with media changes every 2 days. Cells are split regularly (1:5) in order to maintain colonies of undifferentiated HESC.

(This was assessed by staining for the markers SSEA3, SSEA4, TRA-1-60 and TRA-181. Routine screening at the University of Sheffield confirmed that the HESC used were karyotypically normal (Shef1 (46XY) and Shef7 (46XX)).
Differentiation and Expansion of HESC-RPE We have found that hESC-hRPE are reliably formed when hESC colonies are allowed to become superconfluent on a MEFs. When the borders of individual hESC colonies fuse together (10 days post-passage) the media changing regime is changed from once every 2 days to once every day using the basic hESC media detailed above (minus bFGF). This factor was withdrawn from the media because of a documented link between bFGF and repression of RPE specification. Pigmented foci appear in superconfluent hESC cultures between 1-2 weeks following implementation of the daily feeding regime.

Following their formation, pigmented foci are excised mechanically using the tip of a glass pasture pipette and microsurgical blades. This approach is only practical when the foci obtain at least 1 mm in diameter. During this procedure, every effort is made to dissect away surrounding, non-pigmented material prior to placement of pigmented foci onto 35 mm tissue culture dishes coated with growth factor reduced Matrigel™ (BD Biosciences, diluted 1:30) or laminin. A total of 10 pigmented foci are placed in each dish and the RPE cells allowed to expand on matrigel for a further 35 days (i.e. 5 weeks in basic HESC-media minus bFGF). During this phase the media changes are carried out every 2-3 days. This timeframe is sufficient to yield monolayer sheets of pigmented cells ranging from 2-3 mm. Using this method, sheets of RPE (approaching 1 cm) have been maintained in vitro in our laboratory for up to 4 months.

Other differentiation methods and techniques known in the art may be used to produce the cells of interest, including methods to derive RPE cells from khES-1 and khES-3 cell lines (Osakada et al., (2008) Nat Biotechnol, 26, 215-224) and methods to derive RPE from H1, H7 and H9 cells (Klimanskaya et al., (2004) Cloning and stem cells, 6, 217-245).
Human ES Cell Seeding onto Membranes and Subsequent Culture Method
Cell Harvesting:

Using a sterile surgical knife, incisions are made around the pigmented cell clusters to separate them from non-pigmented cell population within the tissue culture flasks. The clusters are then removed using a pipette tip or sterile glass pipette. In some instances, this is done while aspirating simultaneously to help tease them away.

The pigmented clusters are then collected together with their growth media in an eppendorf tube. Following centrifugation at 12,000-13,500 rpm for 3-5 minutes ensuring the clusters are firmly settled, exchange of media with dissociating solution is performed. The dissociating solution is made up as follows: 90% Non-enzymatic Cell Dissociation Solution in PBS without calcium or magnesium (Sigma-Aldrich), and 0.25% Trypsin. The remainder is Dulbecco's Phosphate Buffered Saline without calcium or magnesium. Cell clusters are incubated in this dissociation solution at 37° C. for 5-15 minutes.

Rigourous trituration of the cell clumps is performed with a pipette until the pigment clusters are dissolved. Centrifugation is repeated at 12,000-13,500 rpm for 5 minutes. The dissociation solution is aspirated without disturbing the pellet. Growth media is now added and the cell pellet which is then re-suspended by trituration. Measurement of cell density is done with a haemocytometer at this stage and seeding density is accordingly calculated.
Membrane Preparation:

Membranes are sterilised using a laminar flow hood UV lamp for 30 minutes on either side. They are then placed within a culture dish and a suitable insert is used to weigh them down. Using this setup, the membranes are then coated with 1:30 matrigel (BD Biosciences) at either 37° C. for 30 minutes (thick gel method) or at 4° C. overnight (thin gel method). Laminin has also been used successfully at surface concentration of 1-10 µg/cm². The advantage of Laminin is that human Laminin is commercially available, allowing a xeno-free method which is important for achieving clinical grade standards (Lei et al, 2007).

Figure 1B:
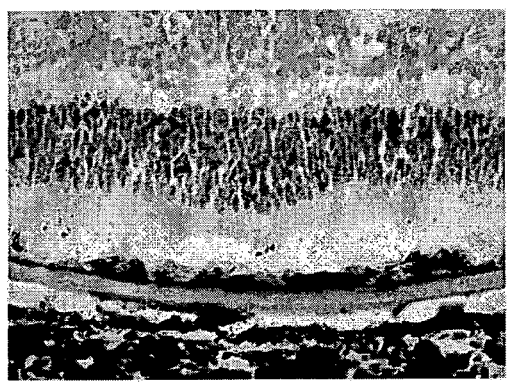
Figure 1C:
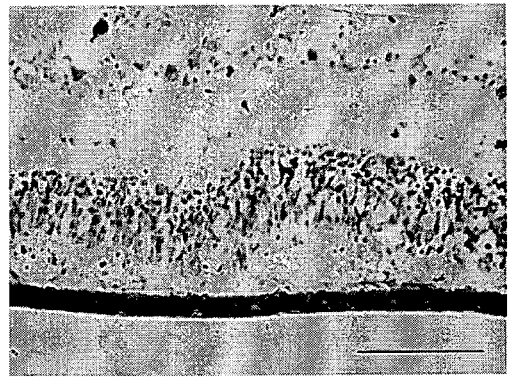
Figure 2A:
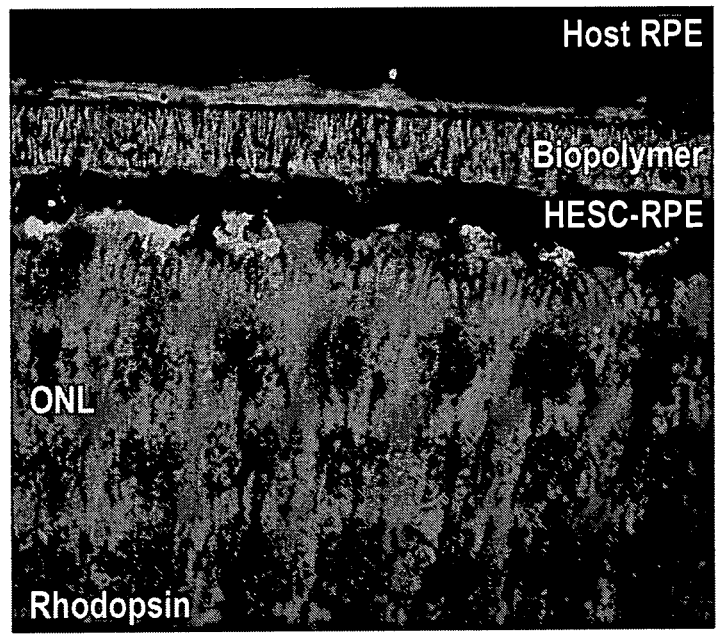
FIG. 2 is a confocal image of HESC-RPE on biopolymer in pig eye, 1 month survival. HESC-RPE form a uniform, pigmented sheet adjacent to pig photoreceptors (rhodopsin, FITC) and overlying the pig RPE. Some photoreceptor material is present within the HESC-RPE cells (A). B shows that donor RPE cells express RPE65 (TRITC). This demonstrates that transplanted HESC-RPE function as normal in-vivo.
Figure 2B:
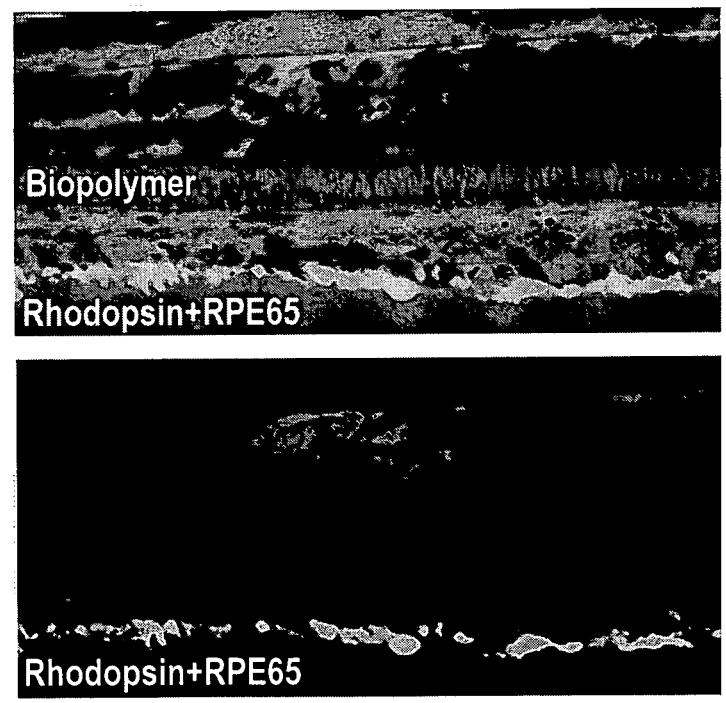
Figure 3A:
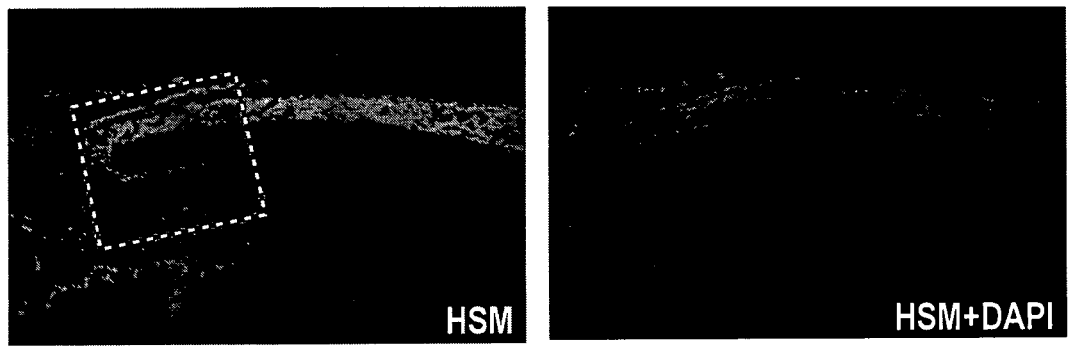
FIG. 3 shows dissociated HESC-RPE transplanted into 3 week-old dystrophic RCS rats after 5 weeks on cyclosporine. The grafted human cells are labelled red with our unique anti-human surface marker (HSM) antibody. The labelled processes of HESC-RPE-derived cells bypass the outer limiting membrane and integrate into the host synaptic layers. The boxed region in A is magnified in B. This demonstrates that transplanted cells were able to maintain a good level of visual function in the transplanted eye (compare to non-transplanted eye from the same animal). Visual acuity using our optokinetic equipment and is reported in cycles per degree (c/d).
Figure 3B:
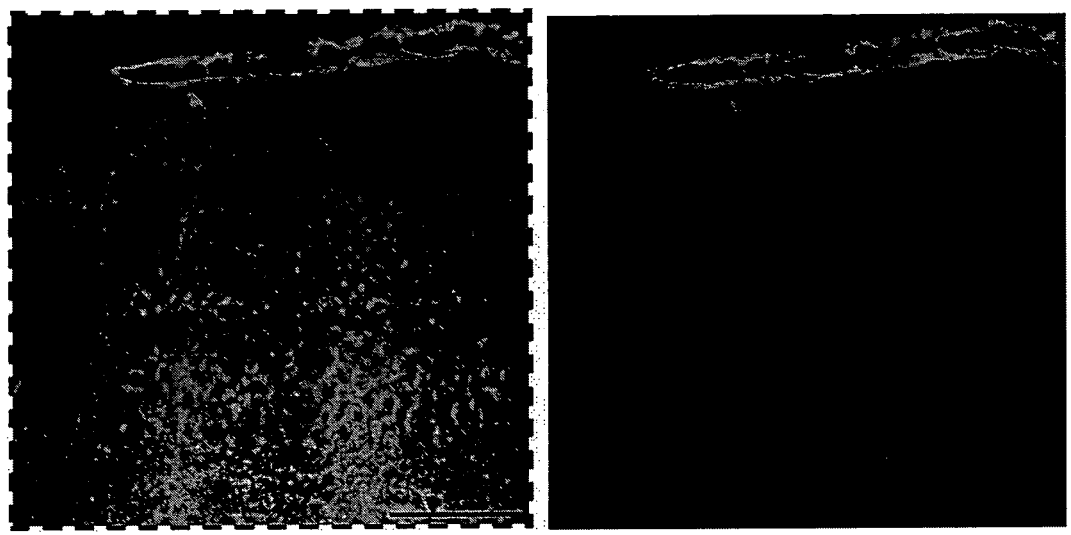
Figure 3B:
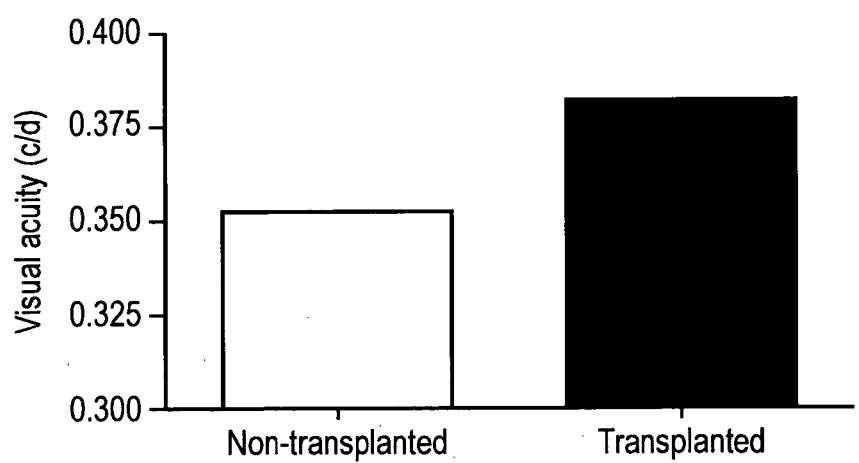

Patches of the membrane have been transplanted into pig eyes and into rat eyes. The results of transplantation are shown in FIGS. 1 to 3. FIG. 1 shows a biopolymer patch with HESC-RPE in situ in the pig eye one month after transplantation. This demonstrates the biocompatibility of the polymer in vivo and that the monolayer of RPE cells is essential to maintain viable photoreceptors FIG. 2 shows an image of HESC-RPE on biopolymer in a pig eye, after 1 month survival. This demonstrates that transplanted HESC-RPE function as normal in vivo.

| Seeding Density (cell/cm²) | Pigmentation As seen with naked eye | Microscopic Examination | |
|---|---|---|---|
| | | No. of Pigmented cells per 40x microscopic field | Regular Morphology (Perfect Hexagon is best = zero)* |
| 70,000 | Nil | 16 | Cells too sparse to calculate |
| 212,000 | Light | >400 | 0.023 |
| 270,000 | Dark (good) | >400 | 0.024 |
| 391,000 | Darkest (best) | >500 | 0.0175 |

Example 3

Growing Cells on Different Membranes

A number of different membranes were tested for ability to support cell growth. The results are given in the following table:

| | TC Polystyrene | PLGA | Teflon (PTFE) | Poly-urethanes | Dacron Polyester |
|---|---|---|---|---|---|
| Pros | Excellent well characterised growth surface | Good growth surface | Strong, flexible, porous | Strong, flexibe, porous | Strong, flexible, sufficiently porous excellent growth surface. Pore size small enough to exclude cell migration of both donor and host immune cells. Excellent surgical handling properties despite being very thin (see thickness) |
| Thickness | Thin film unavailable | 700-900 µm† | 90-150 µm | 60-200 µm | 5-12 µm |
| Pore size | N/A | 17-50 µm | Approx. 0.3-0.5 µm | 20-200 µm | 0.4 µm |
| Pore density | N/A | High | High | Low | $1 \times 10^{8}$ per cm² |
| Hydrophobicity | No | No | Strong | No | No |
| Cell affinity | High | High | Very Low | Low-Medium | High |

FIG. 3 shows dissociated HESC-RPE transplanted into 3 week-old dystrophic RCS rats after 5 weeks on cyclosporine. This demonstrates that transplanted cells were able to maintain a good level of visual function in the transplanted eye (compare to non-transplanted eye from the same animal). Visual acuity was measured using our optokinetic equipment and is reported in cycles per degree (c/d).

Example 2

Seeding Membranes

RPE cells were seeded onto membranes at various densities to find the optimal density of seeding for highly differentiated cells. The cells were observed for the characteristics of RPE cells, such as pigmentation and cobblestone morphology. The results are shown in the following table:

Example 4

RPE Cell Growth

Morphology:
was assessed for the transparent polymers using live image capture on a phase contrast enabled inverted microscope. For non-transparent polymers morphology was assessed by immunostaining for junctional markers (Usually ZO-1)
To Test Cell Growth:
A combination of light microscopy, immunochemistry with confocal microscopy, electron microscopy and cell viability assay was used to assess cell growth.
Cell Viability Assay (Alamar Blue Assay):
Various polyurethane polymers were bound to tissue culture commercial inserts as for PLGA. Briefly, the original filter was excised and the residual material sanded away with sanding paper. Following thorough rinsing with PBS the experimental polymer was mounted on the insert with household cyanoacrylate adhesive (Loctite, Henkel Corporation, Avon, Ohio). To test suitability of polyurethane based polymers an Alamar blue cell viability assay was conducted to measure living cell density as follows: The assay was conducted as follows: Cells are seeded onto the different surfaces at a low density using serum containing media to allow optimum attachment. Cells are incubated at 37° C. for 24 hours to allow sufficient attachment. They are then rinsed twice in serum-free media to wash out unattached cells and then incubated for at least 12-24 hours in serum-free media to synchronise the cells. The cultures are then grown for the desired time period. To take a measurement, cultures are rinsed once in phenol red-free Hank's Balanced Salt Solution (PRF-HBSS) before applying a specified volume of 10% solution of Alamar Blue in PRF-HBSS. The cultures are incubated at 37° C. for 45 mins. The blue supernatant will transform into a fluorescent red colour in proportion to the number of living cells. The supernatants are collected in a 96 well plate and analysed in a plate reader for fluorescence (excitation 530-560 nm emission 590 nm).

Figure 4:
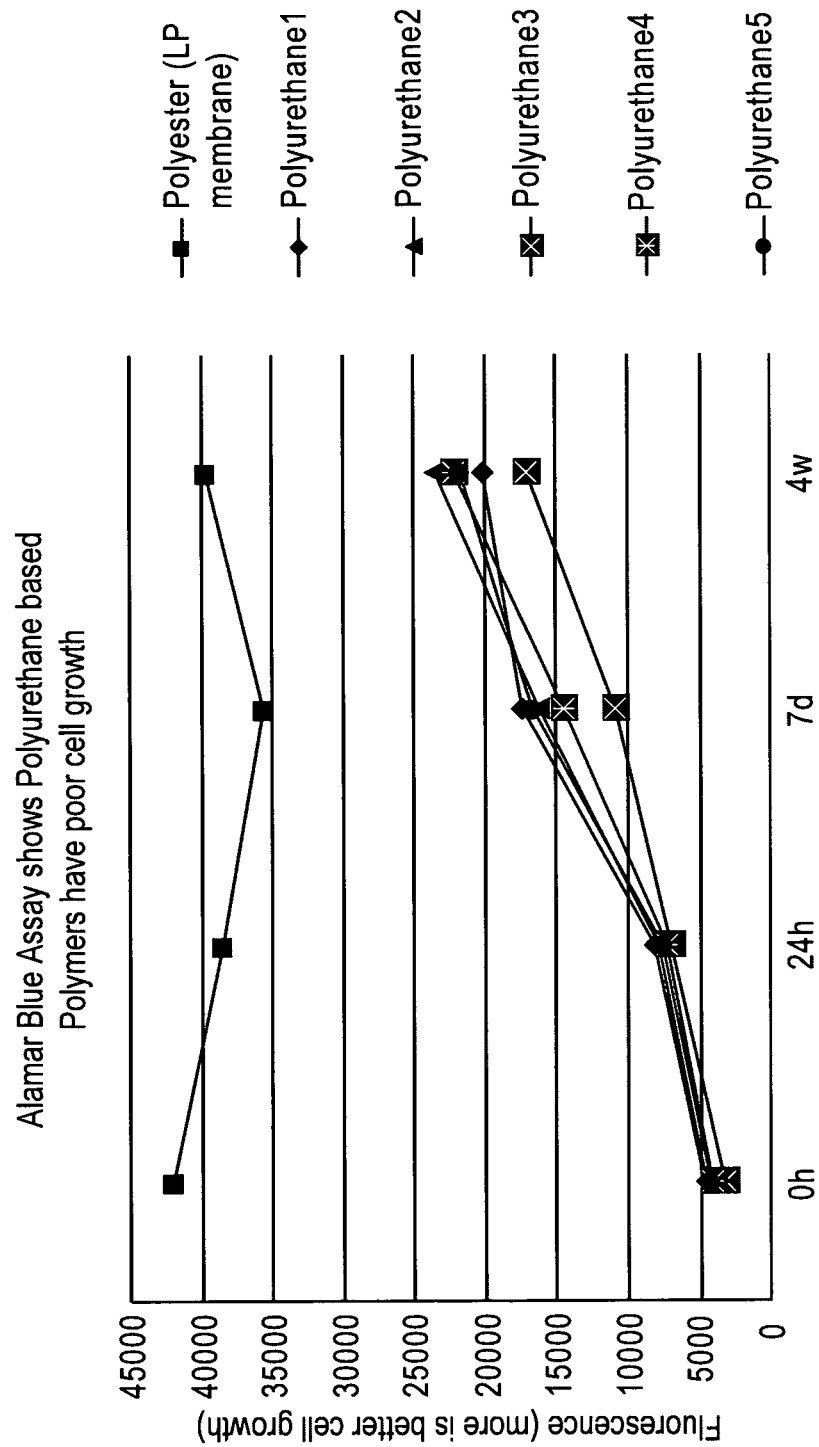
FIG. 4 shows cell growth on a variety of membranes.

The results of the Alamar Blue viability assay for the various materials are shown in the table below. In addition, the cell growth on the polyurethanes and polyester were compared and the results shown in FIG. 4. All the polyurethane based polymers showed reduced cell growth when compared to our polyester filter.

membrane. Mounting was achieved using household cyanoacrylate adhesive (Loctite, Henkel Corporation, Avon, Ohio). These inserts were sterilized by exposure of each side to a UV lamp in a laminar flow hood for 30-60 minutes. Passage 28 ARPE-19 cells were seeded onto the membranes at a density of 90,000 cell/cm$^2$.

In another series, asymmetric PLGA membrane was mounted onto empty inserts (as above). The inserts as well as tissue culture polystyrene dishes (for control) were coated with laminin at standard working concentration (Sigma-Aldrich, derived from the murine Engelbreth-Holm-Swarm tumour). Both dishes and inserts were then seeded with p30 ARPE19 at a higher density of 180,000 cell/cm$^2$ to reduce time to confluence. Cultures were maintained with DMEM High Glucose based RPE media twice per week.

Example 5

Coatings

HESC Culture Methods:

The HESC lines Shef1 and Shef7 were maintained in flasks coated with 0.1% Gelatine and seeded with inactivated mouse embryonic fibroblast (MEF) feeders (Draper et al, 2002). Cells were maintained in basic HESC-medium which is

|  | TC Polystyrene | PLGA | Teflon (PTFE) | Polyurethanes | Commercial culture-grade polyester | Polyester |
|---|---|---|---|---|---|---|
| Cell growth | Excellent | Excellent | Poor | Medium | Excellent | Excellent |
| Morphology | Poor | Poor | N/A | Good | Good | Good |
| Electron Microscopy | — | — | Sparse isolated cells | Detached/curled sheets of cells. This also is further evidence of poor cell attachment | Confluent attached cells | Confluent attached cells |
| Junctional Staining (Confocal microscopy) | Yes | Yes | N/A | Yes (Solid polymer only) | Yes | Yes |
| Polarity Confocal microscopy) | Yes | Yes | N/A | Partial? (Solid polymer only) | Yes | Yes |

These findings were confirmed with immuncytochemistry and confocal microscopy which showed very sparse cellular presence in most of the polyurethane based polymers. In one of the polyurethane based polymers (solid polymer) there was good cell growth and junctional staining but cellular sheets easily detached from the polymer surface.

It is clear from the results of the assay, as shown in the table above, that polyester has significant advantages over other possible membrane materials.

PLGA Methods:

PLGA membranes were a kind gift from E. B. Lavik and R. Langer (Department of Chemical Engineering, MIT, Cambridge, Mass.). PLGA material was originally purchased as Resomer® 503H (Boehringer-Ingelheim, Ingelheim, Germany), and asymmetric PLGA membranes were synthesized as described by these authors (Lu et al, 2000a and 2000b; Lavik et al, 2001 and 2002). This asymmetric profile allows cell attachment to the smooth upper surface while also allowing cells to communicate with the basal environment through the polymer's lower porous side.

PLGA asymmetric membrane was mounted 6.5 mm Corning Transwell® inserts after having removed the original based in High glucose Knockout Dulbecco's Modified Eagle's Medium (DMEM, Invitrogen) with 20% Knockout serum replacement (Invitrogen), 1% non-essential amino acid solution, 1 mM L-Glutamine (Invitrogen), 4 ng/ml human bFGF (Invitrogen) and 0.1 mM β-mercaptoethanol (Sigma). Once removed from cryopreservation, HESC lines were maintained for up to 74 passages with media changes every 2 days. Cells were split regularly (1:4) in order to maintain colonies of undifferentiated HESC.

The following coatings were applied according to their standard manufacturer protocol unless otherwise stated: matrigel (1:30), laminin, collagen IV, Human collagen I, Puramatrix®, plasmanate, poly-L-Lysine, and no coating as control. Briefly, each coating was thawed at 4° C. and diluted in either PBS or serum-free media. Plates/inserts were coated either at 4° C., room temperature, or 37° C. according to each manufacturer's guidelines. Matrix solution was then removed and plates were either washed or air-dried as per standard procedure. HESC-RPE colonies (primary colonies) were excised from culture flasks and placed into media following which they were seeded onto the plates/inserts.

Direct observation of the cultures was used to assess for adhesion of HESC colonies and their spreading. Observation of recently seeded HESC 24 hours upto 72 hours post-seeding revealed that only Matrigel and Laminin resulted in HESC-RPE colony adhesion i.e colonies were well immobilised and not prone to detachment even with rigourous media rinsing. One batch of Human pepsinised placental laminins achieved immobilisation of the HESC-RPE colonies, whereas another batch failed. All the other coatings (Collagen IV, Human Collagen I, Poly-L-Lysine, Puramatrix®, Plasmanate) completely failed in this respect.

Example 6

Culture of RPE from Shef1 HESC

Cell Culture

The Shef1 HESC are maintained in T25 flasks coated with 0.1% Gelatine and seeded with human fibroblast feeders (optimal seeding density of $2.25 \times 10^5$ cells per T25 ($9 \times 10^3/cm^2$)). Cells are maintained in basic HESC-medium which consists of the following components: High glucose (4.8 g/L) Knock-out Dulbecco's Modified Eagle's Medium (DMEM, Invitrogen) with 20% Knockout serum replacement (Invitrogen), 1% non-essential amino acid solution, 1 mM L-Glutamine (Invitrogen), 4 ng/ml human bFGF (Invitrogen) and 0.1 mM β-mercaptoethanol (Sigma). Once removed from cryopreservation, the Shef 1 HESC undergo media changes every 2 days and are split regularly (1:4) in order to maintain colonies of undifferentiated HESC (assessed by staining for the markers SSEA3, SSEA4, TRA-1-60 and TRA-181).

Differentiation and Expansion of HESC-RPE

We have found that HESC-RPE are reliably formed when Shef1 HESC colonies are allowed to become superconfluent on feeders. When the borders of individual HESC colonies fuse together (approx. 10 days post-passage) the media changing regime is altered from once every 2 days to once every day using the basic HESC media detailed above (minus bFGF). This factor was withdrawn from the media because of a documented link between bFGF and repression of RPE specification. Pigmented foci appear in superconfluent HESC cultures between 1-2 weeks following implementation of the daily feeding regime.

Cells were cultured for a further 5 weeks after which pigmented foci were excised mechanically using the tip of a glass pasture pipette and microsurgical blades. This approach is only practical when the foci obtain at least 1 mm in diameter, therefore it may be beneficial to culture cells for longer than 5 weeks. During this procedure, every effort is made to dissect away surrounding, non-pigmented material prior to placement of pigmented foci onto 35 mm tissue culture dishes coated with laminin-1. A total of 10-20 pigmented foci can be placed in each dish and the RPE cells are allowed to expand in 2 ml of medium for a further 35 days (i.e. 5 weeks in basic HESC-media minus bFGF). During this phase the media changes are carried out every 2-3 days. This timeframe is sufficient to yield monolayer sheets of pigmented cells ranging from 2-3 mm.

This method differs from other published protocols as follows: 1. We use a higher standardised concentration of KSR (20% as opposed to 8-15% variable by Lanza group) STATEMENT. 2. We do not use Plasmanate, human LIF or bFGF during the production of RPE cells from super-confluent HESC cultures.

Dissociation and Suspension of HESC-RPE

Pigmented HESC-RPE were harvested from either T25 flasks containing HESC-RPE colonies on feeders (passage 0), or from expanding HESC-RPE sheets on feeders (passage 1). Removal of the cells was by cutting around them with a sterile microblade and dislodging them with sterile pipette tip. HESC colonies/sheets were then aspirated and suspended in HES medium −bFGF (without bFGF) until further use.

The desired amount of clusters is placed along with their growth media in a tube and centrifuged at 2400 to 3600 rpm for 5 minutes to enable the removal of supernatant media. Centrifugation was repeated as necessary to enable exchange of solutions as follows: Cells are washed twice with PBS and then incubated at 37° C. for 20 minutes in 90% Non-enzymatic dissociation buffer in PBS (Sigma #C5914) and 10% Trypsin 10× in PBS (Trypsin from Porcine Pancreas, Sigma; final trypsin concentration 0.25%). Following this period of incubation, cells are triturated thoroughly until completely suspended i.e no visible cell clumps. They are then centrifuged again to enable removal of the dissociation buffer after which the cells are resuspended in HES medium −bFGF and placed in a 37° C. incubator until further use.

Assembly of Polymer Sheets onto Culture Inserts 13 mm polyester filter discs with a pore size of 0.4 μm and pore density of approximately $1 \times 10^8$ pores/$cm^2$ were attached to Transwell inserts in place of the original filters using a biological grade vinyl-based silicone elastomer (Kwik-Sil, World Precision Instruments Inc. Sarasota, Fla.). The inserts were between 5 and 12 μm thick. The polyester had a weight of 1.2 mg/$cm^2$. The inserts were rinsed once in PBS, air-dried, and irradiated with a UV lamp in a laminar-flow hood for 30 minutes each side for sterilisation. Sterilised inserts were then stored in a sterile laminar flow hood.

Coating and Seeding of the Prepared Culture Inserts

Sterilised inserts were coated with 1:30 diluted laminin-1 for 30 minutes at 37° C. Laminin (at a concentration of 43 μg/$cm^2$ and incubated at 37° C. for 30 minutes). Laminin was aspirated immediately before cell seeding. Cell density of the HESC-RPE suspension was measured using a Neubauer® Haemocytometer with Trypan Blue 1:1 dilution. Trypan Blue staining was used to confirm cell viability which was greater than 93% in every case. Cells were seeded at an optimal density of 200,000-400,000 cell/$cm^2$. Seeded cells were allowed to attach for at least 24 hours and typically 48 hours before the first media change. Media was changed 3 times a week thereafter.

The invention claimed is:

1. A membrane for supporting growth of cells, the membrane being non-biodegradable and porous, wherein pores of said membrane are between approximately 0.2 μm and 0.5 μm diameter, wherein pore density of the membrane is between $1 \times 10^7$ and $3 \times 10^8$ pores per $cm^2$, said membrane comprising a layer of retinal pigment epithelial cells, or retinal pigment epithelial cell precursors, or retinal derivative cells formed from the differentiation of retinal pigment epithelial cells on the membrane.

2. A membrane according to claim 1 wherein the membrane hydraulic conductance of the membrane is more than $50 \times 10^{-10}$ in $sec^{-1} Pa^{-1}$.

3. A membrane according to claim 1 wherein the membrane is sterilised by gamma irradiation, ethylene oxide, autoclaving or UV sterilization without degrading.

4. A membrane according to claim 1, wherein the membrane is sealed by ultrasonic sealing, radio frequency sealing or insert moulding.

5. A membrane according to claim 1, wherein said membrane has a maximum thickness of approximately 11 μm.

6. A membrane according to claim 1, wherein said membrane has a maximum weight of approximately 1.5 mg/$cm^2$.

7. A membrane according to claim 1, wherein the membrane is hydrophilic.

8. A membrane according to claim 1, having a pH of 4 to 8.

9. A membrane according to claim 1, comprising a coating on at least one side.

10. A membrane according to claim 9, wherein the coating is laminin, matrigel, fibronectin, or PLGA.

11. A membrane according to claim 9, comprising a pharmacological or biological agent, bound to the coating.

12. A membrane according to claim 1, wherein the cells are human retinal pigmented epithelial cells.

13. A membrane according to claim 12, wherein the cells are immortalised cells.

14. A membrane according to claim 1, wherein the membrane is made from a hydrophilic polymer selected from the group consisting of: a polyester, a polyurethane, a polyurea-urethane, a polyamide, a polyether-ester, a polycarbonate, a polyacrylate, poly(tetrafluoroethene), a polysiloxane, a polyolefin, and polyoxymethylene.

15. A method comprising:
seeding one or more retinal pigment epithelial cells, or retinal pigment epithelial cell precursors, or retinal derivative cells onto a membrane, to form and support at least one colony of cells, wherein the membrane is substantially non-biodegradable and porous and has a maximum thickness of approximately 11 μm, wherein pore density of the membrane is between $1\times10^7$ and $3\times10^8$ pores per $cm^2$ and pores of said membrane are between approximately 0.2 μm and 0.5 μm diameter.

16. A method for using a membrane according to claim 1, comprising:
transplanting the membrane into an eye.

17. A method according to claim 16, wherein the cells are autologous to the eye.

18. A method according to claim 16, wherein the eye is in a patient that has age related macular degeneration.

19. A membrane comprising a substantially non-biodegradable and porous support layer coated on at least one side with a coating comprising glycoprotein, wherein pores of said membrane are between approximately 0.2 μm and 0.5 μm diameter, wherein the pore density of the support layer is between $1\times10^7$ and $3\times10^8$ pores per $cm^2$.

20. A method of seeding cells onto a membrane comprising the step of:
seeding the cells onto the membrane at a density of 200,000 cells per $cm^2$ or greater, wherein pores of said membrane are between approximately 0.2 μm and 0.5 μm diameter, wherein pore density of the membrane is between $1\times10^7$ and $3\times10^8$ pores per $cm^2$, and wherein the cells are retinal pigment epithelial cells, or retinal pigment epithelial cell precursors, or retinal derivative cells.

21. A membrane for supporting the growth of cells, the membrane comprising a polyester and being in the form of a substantially non-biodegradable and porous support layer having a maximum thickness of approximately 11 μm and coated on at least one side with a coating comprising a glycoprotein, the pores being approximately 0.4 μm in diameter, wherein the pore density of the pores in the support layer is approximately $1\times10^8$ pores per $cm^2$; further comprising a layer of retinal pigment epithelial cells, or retinal pigment epithelial cell precursors, or retinal derivative cells formed from the differentiation of retinal pigment epithelial cells on the membrane.

22. A membrane according to claim 14 wherein the hydrophilic polymer is polyester.

23. A membrane according to claim 1 or 21 wherein the membrane comprises a layer of retinal pigment epithelial cell precursors.

24. A membrane according to claim 23 wherein the retinal pigment epithelial cell precursors are human embryonic stem cells.

\* \* \* \* \*